United States Patent [19]

Polita et al.

[11] Patent Number: 5,143,903

[45] Date of Patent: Sep. 1, 1992

[54] METHOD OF TREATMENT WITH TRIPEPTIDE PHARMACEUTICAL COMPOSITIONS AS IMMUNOMODULATORS

[75] Inventors: Vincenzo Polita; Giovanna De Luca; Giovanni Di Stazio; Mario Materazzi, all of Rome, Italy

[73] Assignee: Polifarma S.p.A., Rome, Italy

[21] Appl. No.: 582,168

[22] Filed: Sep. 14, 1990

[30] Foreign Application Priority Data

Oct. 5, 1989 [IT] Italy .................. 48430A/89

[51] Int. Cl.⁵ .......................... C07K 5/06; C07K 5/08
[52] U.S. Cl. .................................. 514/18; 514/19
[58] Field of Search .................................. 514/18, 19

[56] References Cited

U.S. PATENT DOCUMENTS

| 4,428,938 | 1/1984 | Kisfaludy et al. | 514/18 |
| 4,543,350 | 9/1985 | Kondo et al. | 514/18 |
| 4,619,916 | 10/1986 | Di Stazio et al. | 514/18 |
| 4,681,871 | 7/1987 | Teschemacher et al. | 514/18 |
| 4,851,388 | 7/1989 | Bright | 514/18 |

FOREIGN PATENT DOCUMENTS

| 0148133 | 7/1985 | European Pat. Off. | 514/18 |
| 0204374 | 12/1986 | European Pat. Off. | |
| 1186733 | 6/1985 | Italy . | |
| 2091740 | 4/1983 | United Kingdom . | |

Primary Examiner—Lester L. Lee
Attorney, Agent, or Firm—Birch, Stewart, Kolasch & Birch

[57] ABSTRACT

Compounds of peptide nature presenting a sequence of three aminoacids, in particular with PYR and TRP as terminal groups, are found to be active as immunomodulating agents.

6 Claims, No Drawings

METHOD OF TREATMENT WITH TRIPEPTIDE PHARMACEUTICAL COMPOSITIONS AS IMMUNOMODULATORS

BACKGROUND OF THE INVENTION

1. Field of the Invention

The present invention refers to compounds of a peptide nature which show the capability to influence the immune response in mammals.

The polypeptide compounds are identified by the following sequence of aminoacids:

A—X—B in which
- A indicates PYR, PRO, Z-PRO
- B indicates TRP, PHE, TYR, and
- X indicates GLY, VAL, GLU, ASP, SER, ALA, ASN, GLN, ILE, LEU, PRO, LYS and ARG.

The above mentioned compounds, along with their salts and esters, show an immunostimulant or immunodepressant activity, and can therefore be used generally in therapy as immunomodulators.

2. Description of the Prior Art

The above compounds are made up in the first place of a tripeptide structure PYR-X-TRP, in which X has the meaning indicated above, which represents tripeptide compounds already known from EP-B-0148133 and Italian patent 1186733.

According to the present invention it has been found that said tripeptide compounds also show activity as immunomodulating agents.

In the above mentioned patents these tripeptide compounds were evaluated as anti-hypertension or analgesic agents.

It is further known from conventional medicine that snake poisons have the property of stimulating the immune response of the animals and humans bitten. This feature, which is used to the present day for the preparation of vaccines permitting the reduction of damage caused by poisoning, is generally attributed to the fact that in snake poisons are present antigen patterns, capable of stimulating specific and aspecific responses within the immunitary system of the poisoned animal. As regards the specific responses, snake poisons contain numerous toxins which stimulate the production of clearly distinguishable antibodies.

Summary of the Invention

Differently from the above considerations, the present invention is directed to those substances present in snake poisons which are capable of stimulating the aspecific response of lymphocytes and macrophages in the blood of the individuals bitten.

It has in fact been discovered according to the present invention that several short peptides, present in the poison of rattlesnakes of family Viperidae, along with their derivates obtained by chemical synthesis, are capable of stimulating or depressing the immune response of mammal cells, and they could be used therapeutically whenever the immune system is lacking due to aging, chronic infection, tumours, AIDS, viral diseases and the like, or on the contrary when it is desired to reduce the activity, for example in the transplant of organs.

One object of the present invention is therefore the pharmaceutical use as immunomodulators of the tripeptide compounds characterized by the sequence of amino acids indicated above, or their simple salts and esters for administration to mammals, in an effective amount to modulate the immunitary response.

EXPERIMENTAL SITUATION

Hereinbelow is illustrated the experimental pattern developed starting from a plurality of snake poisons (Crotalidae and Viperidae) which, deproteinized, were tested on human T lymphocites, stimulated with four different agents. The amount of cellular proliferation induced was then measured.

As stimulating agents were used Interleukina 2 (growing factor of T lymphocytes), phytohaemoagglutinine (PHA, a mitogenic agent), concavaline A (ConA, another mytogenic agent) and a protein deriving from tuberculosis mycobacterium (PPD, an antigen).

The poisons were then fractionated by chromatography and the fractions thus obtained were in their turn tested on T lymphocites, until no chromatographically pure peptides were obtained.

Said peptides were used to test their immunomodulating activity in correlation to a test on the proliferation of mononuclear cells, the methods and results of which are described herebelow.

Test on the proliferation of mononuclear cells

Mononuclear cells of peripheral human blood (PBMC), provided by healthy volunteers, were purified according to techniques normally used in haematology laboratories, and were finally suspended, at a concentration of 1.000.000/ml in the bed RPMI 1640 (company Flow Laboratories), enriched with 10% of heat inactivated human serum, 2 mM of glutamine and 40 mcg/ml of Gentalyn (from Shering Co.).

The cells were cultivated (100.000/pit) in triplicate on plates of 96 flat-bottomed pits, for a varying number of days according to the activating substances used (6 days for Interleukin 2 and PPD, 3 days for PHA and ConA), in 200 microliters of the suspension bed, in an incubator at 37° C. with 5% $CO_2$. During the last 17 hours of culture the cells were marked with 0,5 microCuries of tritium thymidine (TdR). At the end of the incubation period, the radioactivity present in the cells was gathered on fiberglass filters. Embedded TdR was measured in a beta-radiation counter.

The results are expressed as arithmetic averages of the counts.

On the cells cultivated in this manner the effect of the substances derived from snake poison was tested.

The effect was evaluated according to quality, expressing with +, + + and + + + the substances acting as stimulants (from the least to the most effective), and with −, − − and − − − the substances inhibiting normal cell growth. The inactive compounds were expressed with =.

When the substances showed a biphase trend with the decrease of the dose set to incubate (which is not uncommon in immunomodulators), this has been indicated by separating with / the effects of the higher doses from those of the lower doses.

The results of the test described above, obtained by evaluation of deproteinized snake poisons, or fractions thereof, are shown in the following table 1.

TABLE 1

| POISON | ACTIVATOR USED | | | |
|---|---|---|---|---|
| | Interl. 2 | PHA | ConA | PPD |
| Ankistr.Bilineatus | --- | = | | = |
| Ank.Cont.Mokason | -- | -/+++ | ---/+ | --/++ |
| Ank.Pisc.Piscivorus | --- | ---/+ | --- | --- |
| Bitis Gabonica | | --/+++ | -/+ | |
| Bothrops Jararaca | | -- | --- | |
| Bothrops Neuwedii | | - | -- | |
| Crotalus Atrox | | --/+ | --- | |
| Crot.Horr.Atricaudatus | --/+ | --/+ | | --- |
| Crot.Virid.Oreganus | --- | --- | .--- | |
| Trimeres.Albolabris | ---/+ | -+ | | --- |
| Vipera Ammodytes | -- | - | | --/+ |
| Ank.Bilin. fraction 1 | --- | --- | | --- |
| Ank.Bilin. fraction 2 | -/+ | | | -- |
| Ank.Bilin. fraction 3 | = | ---/+++ | | = |
| Ank.Bilin. fraction 4 | = | = | | |

The results of the table clearly show that the majority of the deproteinized poisons which underwent the test, react by suppressing the immune response of the human mononuclear cells. It is clear furthermore that the progressive purification of the poisons causes the isolation of compounds with an increasingly evident effect on the immune response (activation or inhibition).

Experimental evidence for the present invention

The previously illustrated experimental test shows that peptides derived directly from snake poisons have a mainly suppressive immune response which is furthermore of an opposite sign on variation of the dosage.

The compounds of the present invention show on the contrary a clear stimulating or inhibiting response of the immunological activity of human T lymphocytes.

The test previously described was repeated using, in the place of the poisons obtained by chromatography, synthetic peptides according to the present invention.

A hexapeptide PYR-LEU-TRP-MET-ASP-PHE was synthetized which, along with the tripeptide sequence PYR-LEU-TRP, also possesses the terminal sequence of cholekystokinin. This sequence seems to possess specific receptors on many types of cell, as described, for example, in Nature 284,33-38, 1980. As structure-activity studies performed on numerous other compounds having the tripeptide MET-ASP-PHE have evidenced the fact that this tripeptide has no influence on biological activity, the tests were focalized on the compound PYR-LEU-TRP and on similar tripeptides already synthetized in precedence.

EXAMPLE 1

Test on the proliferation of mononuclear cells

Using the same methods employed in the test described above, a series of compounds having a peptide structure according to the invention, along with other control compounds, were tested for their imunomodulant activity.

The results are shown in the following table 2:

TABLE 2

| PEPTIDE | ACTIVATOR USED | | |
|---|---|---|---|
| | Interl. 2 | PHA | PPD |
| PYR—LEU—TRP—PRO—ARG—PRO—GLN—ILE—PRO—PRO | ++ | = | = |
| PYR—ASN—TRP | + | - | -/+ |
| PYR—LEU—TRP—MET—ASP—PHE | = | -- | +++ |
| PYR—LEU—TRP | +++ | | +++ |
| Z—PRO—LEU—TRP | +++ | | -/ |

TABLE 2-continued

| PEPTIDE | ACTIVATOR USED | | |
|---|---|---|---|
| | Interl. 2 | PHA | PPD |
| | | | ++ |
| PYR—GLY—PHE | +++ | | -/+ |
| Formyl-MET—LEU—PHE | | | -/+ |
| Phosphoramidon (Sugar-LEU—TRP) | +++ | | +++ |
| Tuftsin (THR—LYS—PRO—ARG) | = | = | = |

The results of table 2 show that the compounds according to the present invention are good stimulators of the immunological response, especially when tested on human mononuclear cells in the presence of Interleukin 2 or of PPD.

The comparison with Phosphoramidon, a compound produced from mushrooms and used in protease inhibition tests, indicates that probably the C-terminal residue LEU-TRP is the one responsible for the immuno-potentialization effect, but that other dipeptides can perform the same function.

A series of experimental confirmation tests on the immune response in vitro and in vivo were performed with the compound PYR-LEU-TRP.

EXAMPLE 2

Effect of PYR-LEU-TRP on the proliferating response of PBMC

The entity of response by human peripheral blood mononucleate cells (PBMC) after stimulation with PPD and with the peptide PYR-LEU-TRP was evaluated on 10 different samples of blood from healthy volunteers.

The results indicate that, using the antigen in optimal doses (10 mcg/ml) and the peptide in two different doses (1 and 0,01 mcg/ml), the proliferative response is always increased, although by an amount varying greatly from one individual to another. The average value of tritium thymidine incorporated by the cells is roughly doubled both at lower and higher doses.

EXAMPLE 3

Effect of PYR-LEU-TRP on B lymphocytes

Starting from the assumption that the effect of the peptide was due to the stimulation at the time of appearance of the antigen, the B lymphocytes were separated from the T lymphocytes and then were incubated with the peptide before stimulation with PPD.

After washing, the B lymphocites were put into contact with the T lymphocites and the response was evaluated by the counting of tritium thymidine.

The results are shown in the following table 3.

TABLE 3

| Effect on B lymphocites | |
| --- | --- |
| mcg/plate | Incorporation of [$^3$H] TdR |
| 100 | 2.000 |
| 10 | 21.700 |
| 1 | 20.000 |
| 0,1 | 26.000 |

Table 3 shows in an evident manner that the tripeptide presents a strong effect of stimulation of the proliferative response in a concentration range of 1 and 10 mcg/plate, while it is inactive outside this range of concentration.

EXAMPLE 4

Effect of PYR-LEU-TRP in relation to the number of lymohocites

As the diseases due to lack of immune response very often depend on the lack of lymphocites capable of responding adequately, the tripeptide PYR-LEU-TRP was tested on cultures containing greatly varying levels of lymphocites.

The results obtained evaluating the percentual increase of incorporated thymidine underline the fact that the potentialization of the immune response is much more evident when the lymphocites are scarce, while it tends towards zero for very high numbers of cells. This indicates that the compound can have an important role in the case of lymphocite deficiency.

EXAMPLE 5

Effect of PYR-LEU-TRP on macrophages

The results are shown in the following table 4.

TABLE 4

| Effect on macrophages | |
| --- | --- |
| mcg/plate | Incorporation of [$^3$H] TdR |
| 100 | 9.600 |
| 10 | 7.600 |
| 1 | 14.900 |
| 0,1 | 9.150 |
| 0,01 | 6.700 |

The results indicate that, in this case also, there exists a range of concentration in which the peptide is capable of stimulating the proliferative response, whereas outside this range the response is absent. It can thus be said that the tripeptide is an immuno-modulator.

EXAMPLE 6

Effect of PYR-LEU-TRP on the release of Interferon

With the aim of more detailed study of the mechanism of immunitary stimulation, research has been carried out on the quantity of Interferon gamma present in the lymphocites stimulated with 100 mcg/ml of PYR-LEU-TRP. In spite of the variability of the results obtained in the different tests, the tripeptide has been shown to induce an approximately quadruple production of Interferon respect to unstimulated cells.

EXAMPLE 7

Comparison between PYR-LEU-TRP and Interferon gamma

With the aim of more detailed study of the mechanism of action, the effect of the tripeptide PYR-LEU-TRP has been compared to that of Interferon gamma as regards the stimulation of the proliferative response of T lymphocites after presentation of the B lymphocites treated with PPD.

The results indicate that both the tripeptide (used at a dose of 10 mcg/ml) and the gamma Interferon (used at a dose of 1000 u/ml) increase approximately two and a half times the basal response. What is more the two compounds do not have an additive effect, so that it can be assumed that the immunitary response is stimulated by the tripeptide, at least in part, through production of Interferon.

EXAMPLE 8

In vivo tests with PYR-LEU-TRP

The tripeptide PYR-LEU-TRP underwent initial tests in vivo, to confirm its immuno-potentialization activity.

A first experimental model, in which was mainly evaluated the functionality of the B component of the immune response (immunization using ram erythrocytes), showed that the tripeptide, at the doses of 100 and 500 mcg/mouse/i.v., is capable of stimulating in a statistically significant manner the immune response to a successive "challenge" with suboptimal quantities of antigen. If the animal is treated with optimal quantities of antigen (which on their own bring about an optimum immune response), in this case also a potentialization of the immune response can be seen following treatment with the tripeptide, but in this case the increase does not reach statistical significance.

In a second experimental model, used to evaluate the T component of the immune response (infection with Calmette-Guerin bacillus), a significant potentialization of the immune response was also evidenced following repeated treatment with 100 mcg/mouse of tripeptide. In this case the response of animals rendered immunodepressed by the endovenous treatment of the antigen, increased significantly after administration of the tripeptide, which brought the values of the immune response back towards normality.

These results indicate that the peptide PYR-LEU-TRP is capable of increasing both the B component and the T component of the immune response.

Similar results of immunomodulating activity are shown by the tripeptides of the series PYR-X-TRP where X has the meaning indicated above, with or without the addition of the sequence MET-ASP-PHE.

We claim:

1. A method for modulating the immune response in a mammal comprising administering to said mammal a therapeutically immuno-modulating effective amount of a tripeptide compounds of formula

in which
A indicates PYR, PRO, Z-PRO,
B indicates TRP, PHE, TYR,
X indicates GLY, VAL, GLU, ASP, SER. ALA, ASN, GLN, ILE, LEU, PRO, LYS and ARG; or pharmaceutically acceptable salts or pharmaceutically acceptable esters of said compound.

2. A method as claimed in claim 1, in which said compound is PYR-LEU-TRP.

3. A method as claimed in claim 1 or 2, in which said compounds are in the form of their pharmaceutically acceptable salts or pharmaceutically acceptable esters.

4. The method according to claim 1, wherein said compound is a member selected from the group consisting of PYR-ASN-TRP; PYR-GLY-PHE; PRO-LEU-TRP and Z-PRO-LEU-TRP.

5. A method for modulating the immune response in a mammal which comprises administering to said mammal a therapeutically immuno-modulating effective amount of a tripeptide compound selected from the group consisting of PYR-LEU-TRP; PYR-ASN-TRP: PYR-GLY-PHE; PRO-LEU-TRP and Z-PRO-LEU-TRP, or a pharmaceutically acceptable ester or pharmaceutically acceptable salt thereof.

6. A method for modulating the immune response in a mammal which comprises administering to said mammal a therapeutically immune-modulating effective amount of a tripeptide compound of the formula

A—X—B wherein
  A is PYR, PRO or Z-PRO;
  B is TRP, PHE or TYR; and
  X is ASN, GLY or LEU; or a pharmaceutically acceptable ester or pharmaceutically acceptable salt thereof.

* * * * *